United States Patent [19]
Rudolph

[11] 4,196,630
[45] Apr. 8, 1980

[54] OVERHEAD ARM ASSEMBLY

[76] Inventor: Dale C. Rudolph, 6883 Hillpark Ave., Parker, Colo. 80134

[21] Appl. No.: 907,408

[22] Filed: May 18, 1978

[51] Int. Cl.² ............................................ G01N 29/00
[52] U.S. Cl. ...................................... 73/633; 128/660
[58] Field of Search ................. 73/618, 621, 624, 625, 73/633, 634; 128/2 V; 250/445 R, 445 T, 446, 522, 523, 524, 525

[56] References Cited

U.S. PATENT DOCUMENTS

| | | | |
|---|---|---|---|
| 1,423,924 | 7/1922 | Edwards | 250/525 |
| 2,408,500 | 10/1946 | West | 212/49 |
| 2,866,101 | 12/1958 | Wagner et al. | 250/523 |
| 3,396,931 | 8/1968 | Eckstein | 248/280 |
| 3,743,049 | 7/1973 | Levrini | 182/2 |
| 3,777,740 | 12/1973 | Hokanson | 73/621 X |
| 3,924,452 | 12/1975 | Meyer et al. | 73/621 |
| 3,984,693 | 10/1976 | Tomita et al. | 250/445 T |
| 3,996,792 | 12/1976 | Kubota et al. | 73/611 |
| 4,052,888 | 10/1977 | Brown et al. | 73/625 |
| 4,065,976 | 1/1978 | Taenzer et al. | 73/633 |

OTHER PUBLICATIONS

Buchanan & Hastings–Ultrasonic Flaw-Plotting Equipment–Nondestructive Testing, Sep.–Oct. 1955, pp. 17–25.
Watertown Arsenal Laboratory Report, Buchanan & Hastings, pp. 12–16 and FIG. 3–Jul. 27, 1955.

*Primary Examiner*—Charles A. Ruehl
*Attorney, Agent, or Firm*—Fay & Sharpe

[57] ABSTRACT

An overhead arm assembly particularly suited for selectively positioning ultrasonic medical diagnostic equipment. The assembly is comprised of three interconnected pivot arms having both dynamic and static counterweights and arranged so that the outermost or third arm is always vertically oriented. A work element manipulation assembly is rotatably mounted to the third arm adjacent the distal end thereof and a scan arm assembly is mounted to the manipulation assembly. The manipulation assembly includes means for setting the angular orientation of a plane in which the scan arm assembly is constrained and means for selectively shifting the scan arm assembly to other, parallel planes of constraint. The scan arm assembly is dynamically counterweighted and is comprised of pivotally interconnected scan arms which carry a work element such as an ultrasonic transducer.

13 Claims, 6 Drawing Figures

OVERHEAD ARM ASSEMBLY

BACKGROUND OF THE INVENTION

This invention relates to overhead arm assemblies for supporting depending equipment and more particularly to arm assemblies for supporting and selectively locating such equipment relative to some associated body or member.

The invention is particularly applicable to use with medical ultrasonic diagnostic apparatus and will be described with particular reference thereto. However, it will be appreciated that the invention has broader applications in other fields which require exacting placement with each movement of some sensing apparatus or a work element. One such alternative application would be for use in conjunction with engraving apparatus.

In ultrasonic medical diagnostics, images of internal areas of a patient are obtained by transmitting ultrasonic energy into the patient and monitoring the ultrasonic echoes. A so-called planar slice of the patient is most commonly examined. The examination is typically accomplished by utilizing a single probe element which both transmits ultrasonic energy and receives the echoes. By monitoring the position and orientation of the probe as it is moved to various points along the line of intersection between the planar slice and the surface or body of the patient, signal processing equipment can transform the position data and echoes into a representation of the examined planar slice. An example of such processing equipment is shown in U.S. Pat. No. 3,036,390.

The ultrasonic probe is normally carried by an arm assembly defined by a plurality of moveable, jointed arms. These arms are constrained to movement within a single plane, i.e., the plane of the patient slice which is to be examined. Prior arm assemblies have generally comprised a plurality of pivotally interconnected arms such as is shown in U.S. Pat. No. 3,924,452, a plurality of linearly, slideably jointed arms such as is shown in U.S. Pat. No. 3,036,390 or a combination of these two arrangements. The designs of these and other prior arm assemblies have been such that there were problems in accurately selecting the plane of examination. Some prior assemblies were also lacking in adjustment flexibility and required movement of the patient for purposes of changing the plane of examination.

More particularly, and in practical application, doctors often wish to obtain and view more than one planar slice of a patient. These plural slices are most reliably diagnosed if they are parallel and spaced apart by known increments. In prior arm assemblies, especially those which required patient movement for changing the plane of examination, movement to parallel planes was usually arduous and imprecise. Even in the selection of an initial or first plane, alignment of the plane of interest in the patient and the scan plane of the arm was often haphazard and imprecise.

Another problem encountered with prior arm assemblies is that they have been awkward to operate. In some prior assemblies, the scan arms have not been counterweighted or if counterweighted, they have been done so in a crude and inaccurate manner. Often the arms have been constructed of lightweight materials and without proper counterweighting which required the operator to exert different amounts of force to produce the same scanning movement in different portions of the scan plane. This problem resulted in undesired degradation of the visual image being produced.

The present invention contemplates new and improved apparatus which overcomes all of the above referred to problems and others and provides an overhead arm and scanning assembly which is flexible, easy to use, and precisely oriented.

SUMMARY OF THE INVENTION

In accordance with the present invention, there is provided a multijointed overhead arm assembly having a first arm pivotally mounted adjacent one end to a base with a second arm pivotally mounted adjacent one end thereof to the other end of the first arm. A dynamic counterbalancing assembly is operably associated with the first and second arms for applying a counterbalancing force to the first arm about its pivotal connection with the base and which counterbalancing force varies with the angular orientation of the second arm relative to the base. A static counterbalancing may also be provided for the first arm which varies in counterbalancing force in response to the angular orientation of the first arm relative to the base.

In accordance with another aspect of the present invention, a third arm is pivotally mounted adjacent one end thereof to the outermost end of the second arm. The third arm is adapted to support dependent equipment at the distal end thereof and may include orientation means for constraining the third arm movement to a fixed angular orientation relative to the base.

In accordance with still another aspect of the present invention, a manipulation means is operably associated with the distal end of the third arm which constrains a scan arm or other work element to motion through a single predetermined plane. Positioning means associated with the manipulation means facilitates locating the precise position of the plane.

In accordance with yet another aspect of the invention, displacement means allow selective adjustment of the scan arm or other work element from motion through an initial plane to motion through other planes spaced from and parallel to the initial plane.

Among the benefits derived from the present invention is the ease and accuracy with which a work element, such as an ultrasonic probe or the like can be positioned relative to a patient or other target. A probe mounted on a scan arm assembly which is constrained to planar motion can have its plane of motion rotated or incrementally displaced. As a result it is possible to produce a series of cross sectional images of a patient precisely along preselected planes and to have each of the series of images represent parallel planes with known interplanar displacement.

A further benefit of the present invention resides in the simplicity and ease with which the equipment may be moved and positioned. A work element can be smoothly movable by an operator since the overhead arm assembly itself can be easily and continuously positioned to accommodate the work element relative to its target. Improved scanning images are obtained from ultrasonic equipment mounted on the subject overhead arm assembly due to a lessening of operator fatigue and the provision of smooth, effortless scannning and positioning movement.

Yet other benefits will become readily apparent from an understanding of the invention as described hereinafter with reference to the preferred embodiment.

BRIEF DESCRIPTION OF THE DRAWINGS

The invention may take physical form in certain parts and arrangements of parts, a preferred embodiment of which will be described in detail in this specification and illustrated in the accompanying drawings.

DESCRIPTION OF THE PREFERRED EMBODIMENT

Figure 1:
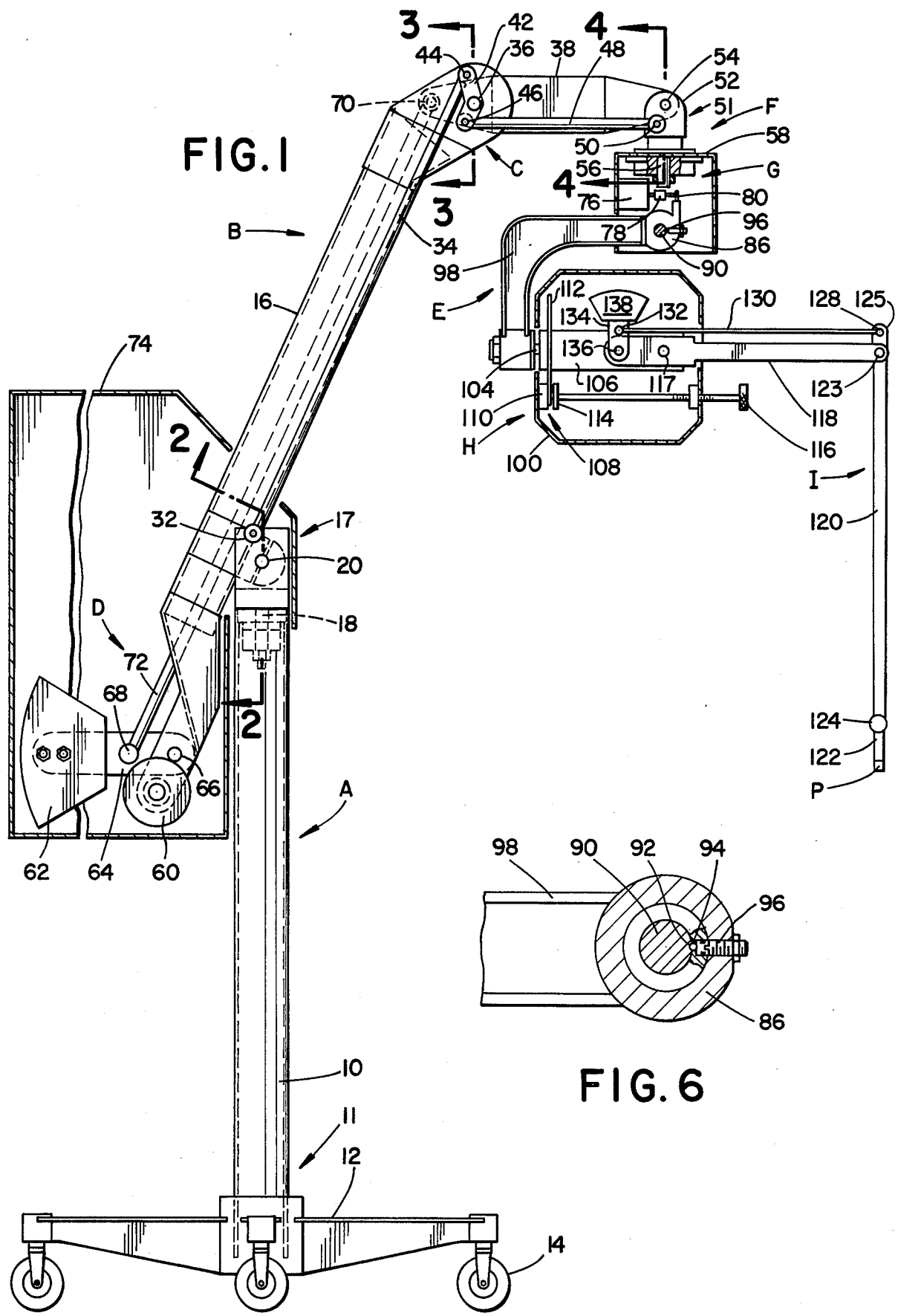
FIG. 1 is a side elevational view of the overall overhead arm assembly with portions of some components removed for ease of illustrating the invention.

Referring now to the drawings wherein the showings are for purposes of illustrating the preferred embodiment of the invention and not for the purposes of limitation, the FIGURES show an overhead arm assembly used in conjunction with ultrasonic diagnostic apparatus. While this is the preferred use for the subject invention, it will be appreciated that it can be readily adapted to use in any number of other environments.

More particularly, FIG. 1 shows a base A having an overhead arm assembly B mounted thereto. This assembly generally includes an orientation means C, a counterweight assembly D and a manipulating assembly E. The orientation means controls the suspended orientation of manipulating assembly E relative to base A. Associated with the manipulating assembly is a rotational coupling F, a horizontal incremental displacement assembly G, an angular orientation selection means H and a multijointed scan arm assembly I. The scan arm assembly is desirably constrained for motion within a single scan plane and the manipulation assembly allows this scan plane to be rotated about a vertical axis in a yaw plane, displaced linearly perpendicular to the plane of FIG. 1 and rotated about a horizontal axis in a roll plane.

With continued reference to FIG. 1, it will be seen that base A includes an elongated vertical column 10 which is securely mounted relative to the floor. Positional stability for column 10 may be provided by many alternative arrangements although the preferred embodiment contemplates one end of the column being fixedly attached by convenient means as at 11 to a base plate 12. The base plate is provided with suitable castors 14 to enable the overhead arm assembly and attendent equipment to be easily brought to the patient or object to be examined.

Arm assembly B which includes a first or main arm 16 is mounted adjacent the other end of column 10 at a first joint generally designated 17 having two degrees of freedom. The first degree of freedom is derived from rotational movement about a pivot pin 18 in what is termed as a yaw plane and the second degree of movement is derived from rotational movement about another pivot pin 20 in what is termed as a pitch plane.

Figure 2:
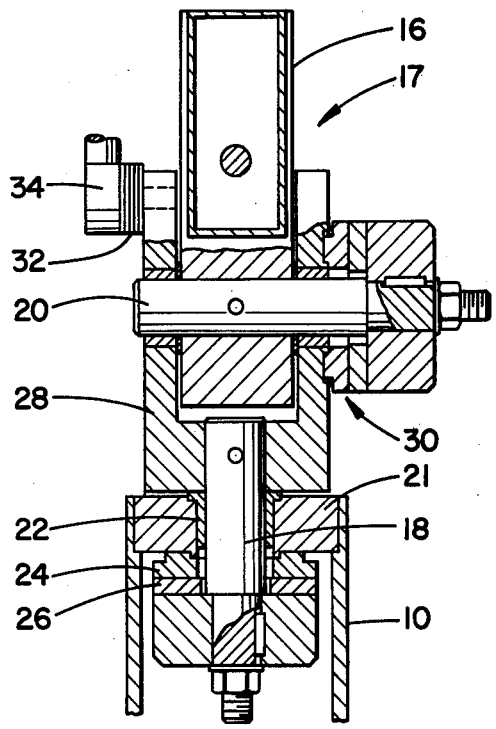
FIG. 2 is a cross-sectional view taken along lines 2-2 of FIG. 1.

FIG. 2 shows the details of first joint 17. Mounted at the top or uppermost end of column 10 is an end cap 21 which receives a bushing 22 which, in turn, receives and locates pin 18 in a generally vertical disposition. Attached to the underside of end cap 21 is a first brake plate 24 adapted to frictionally cooperate with a second brake plate 26 conveniently affixed to pin 18. The first friction brake arrangement defined by brake plates 24,26 is designed to have a high torque, yet require a small amount of space. This type of brake arrangement allows first arm 16 to be moved through a continuum of positions as may be desired. A tooth-type of brake assembly could also be advantageously employed if desired. Such a brake would be somewhat more restrictive in that it would allow the arm to assume a large, but finite number of positions.

Pin 18 is attached to a clevis member 28 which is designed to receive appropriate bushings for receiving and supporting pin 20 in a generally horizontal disposition. Pin 20 is rigidly attached to main arm 16 so that it rotates therewith. A second brake arrangement generally designated 30 provides braking movement of the main arm 16 relative to base A. Brake 30 is located between pin 20 and clevis member 28 and is constructed in a manner similar to the first brake described hereinabove. Clevis member 28 carries a second pivotal connection 32 to mountingly accommodate a linear link 34 for a first orientation connecting means which comprises an element of orienting means C. Means C will be described in more detail hereinbelow.

Figure 3:
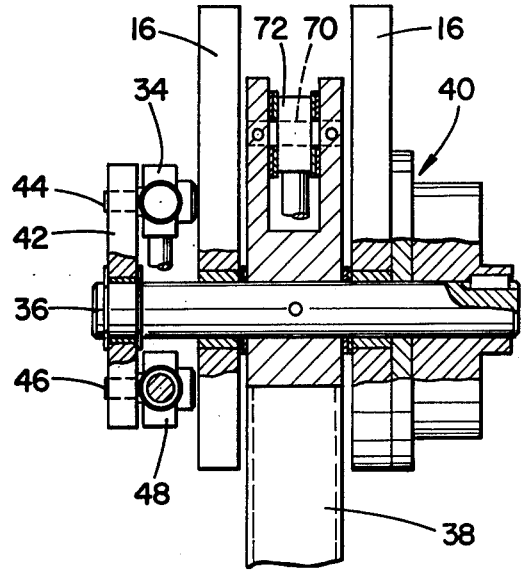
FIG. 3 is a cross-sectional view taken along lines 3-3 of FIG. 1.

Referring to FIGS. 1 and 3, arm 16 is drilled adjacent thereof spaced from first joint 17 to receive a pivot pin 36 which allows movement of the second arm relative to first arm 16 in the pitch plane. Pin 36 pivotally connects a second arm 38 of the overhead arm assembly to first arm 16 and is fixed to rotate with the second arm. Also operably interconnected with pin 36 and arm 16 is a third brake arrangement generally designated 40 constructed in accord with the first and second frictional brakes. An intermediate orientation means including a lever or bell crank 42 is rotatably mounted to pin 36 on the opposite end thereof from brake 40 and comprises a portion of orienting means C. Linear link 34 is pivotally connected at one end of bell crank 42 by a pin 44 and, as noted above, is also pivotally connected to clevis member 28 by pin 32 (FIG. 2). A linear link 48 for a second orientation connecting means is connected to the other end of the bell crank by a pin 46.

Figure 4:
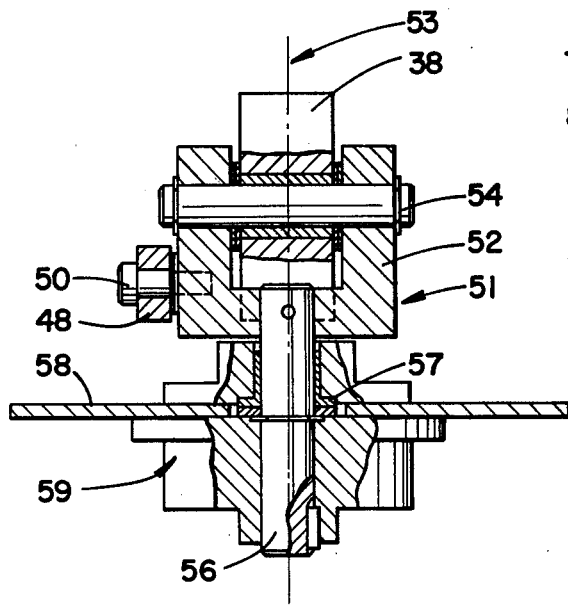
FIG. 4 is a cross-sectional view taken along lines 4-4 of FIG. 1.

As shown in FIG. 1, link 48 extends from the bell crank to a pivotal connection 50 located on the terminal or third arm 51 of overhead arm assembly B. Pivot connection 50 is on a clevis member 52 which comprises a part of the third arm. Terminal or third arm 51 which is shown in more detail in FIG. 4 has a central axis 53 along its length and is pivotally connected to the outermost end of second arm 38 through clevis member 52 by means of a pivot pin arrangement 54. The pivot pin is generally horizontally disposed to allow movement of the third arm in the pitch plane relative to first and second arms 16,38.

Orientation means C includes a first parallelogram having the corners thereof defined by pins 20, 32, 44 and 36 with the opposite sides constrained to a parallel relationship with each other. The orientation means further includes a second parallelogram defined at its corners by pins 36, 46, 50 and 54 wherein the opposite sides are again constrained to a parallel relationship. Further, bell crank 42 which forms one side of each parallelogram acts as an intermediary to constrain the two parallelograms in a fixed relationship.

Using known geometric relationship, it will be seen that when there is relative movement between first and second arms 16, 38 or between arm 16 and column 10, the sides of the two parallelograms pivot about their corners. However, as the sides of the parallelograms pivot about their corners, the relative position of the pair of sides of each parallelogram interconnected by bell crank 42 remains fixed. That is, the side of the first parallelogram defined between pins 20 and 32, will remain in a fixed relationship with the side of the second parallelogram defined between pins 50 and 54. Thus, by selecting the appropriate relative positions for pivot pins 20, 32 and for pivot pins 50, 54, the central axis of terminal or third arm 51 may be maintained parallel to a vertical axis or in any other desirable orientation relative to the floor or to column 10. It will be appreciated that other specific arrangements for controlling the orientation of the terminal or third arm relative to the base could also be used. For example, gear wheels could be placed at pivots 20, 36 and 54 with flexible chains replacing the rigid links.

Referring again to both FIGS. 1 and 4, it will be seen that rotational coupling F facilitates rotation of manipulating means E about the central axis terminal arm 51 and includes a generally vertically disposed pivot pin 56 rigidly attached to clevis member 52. Pin 56 is rotatably mounted in a bushing 57 which is attached to a housing 58 of the displacement means G. A friction brake 59 of the type generally described above restrains the rotational movement displacement means G about pin 56 in a yaw plane.

The counterweight assembly D illustrated in FIG. 1 includes static and dynamic counterweights. The static counterweight 60 is affixed to first arm 16 at the end thereof most adjacent joint 17, i.e., the lowermost or inner end of the arm. The dynamic counterweight includes a biasing means such as weight 62 mounted at the end of a lever 64 which itself is pivotally connected to first arm 16 by means of a pin 66. A linkage arrangement generally designated 72 defines a first counterweight connecting means. This linkage is pivotally connected to second arm 38 by a pin 70 and to lever 64 by a pin 68. It will be seen that pins 36, 66, 68 and 70 thus define the corners of a parellelogram. The longitudinal axis of lever 64 passes through pins 66, 68 and the longitudinal axis of second arm 38 passes through pins 36, 70. These axes form a pair of opposing parallelogram sides and accordingly, will be constrained in a parallel relationship to each other. Therefore, as arm 38 is pivoted about pin 36, lever 64 will be caused to pivot about pin 66 the same amount for causing the counterbalancing effect of assembly D to change as second arm 38 changes its angular orientation in space. Although the preferred embodiment here under discussion contemplates restraining lever 64 and arm 38 to a parallel relationship, it may be desirable in some circumstances to use other relationships. For some applications, it may be operationally advantageous to convert the dynamic counterweight assembly into a nonlinear application biasing means.

It will be appreciated that there will be many weight combinations between weights 60, 62 which will cause the arm to properly balance in the manner desired. One possible weight combination is that weight 60 be selected to cause main arm 16 to be balanced about pin 20. If lever arm 64 has the same weight as second arm 38 and has a length equal to the distance from pin 36 to pin 54, weight 62 would be selected to have the same mass as terminal arm 51 and manipulating assembly E depending from pivot pin 54. In this way, first or main arm 16 would be balanced about its pivotal connection with base A with both ends of the arm subjected to the same application of mass at the same lever arm length. It will be appreciated, however, that counterbalancing can be achieved by shortening lever 64 and increasing weight 62 or vice versa. Further, other distributions of weight between weights 60, 62 may be used along with changes in the position of weight 60 relative to the axis defined by pins 20, 36. One guideline for adjusting the relative weights and lever arm lengths is to maintain the moments of inertia about pins 66, 36 substantially constant about pin 20. Another guidelne is to maintain the product of the mass and length of lever arm about the pivots substantially constant. A fabricated housing 74 is mounted on column 10 to advantageously shield persons from contact with counterweight assembly D and the end of arm 16.

Figure 5:
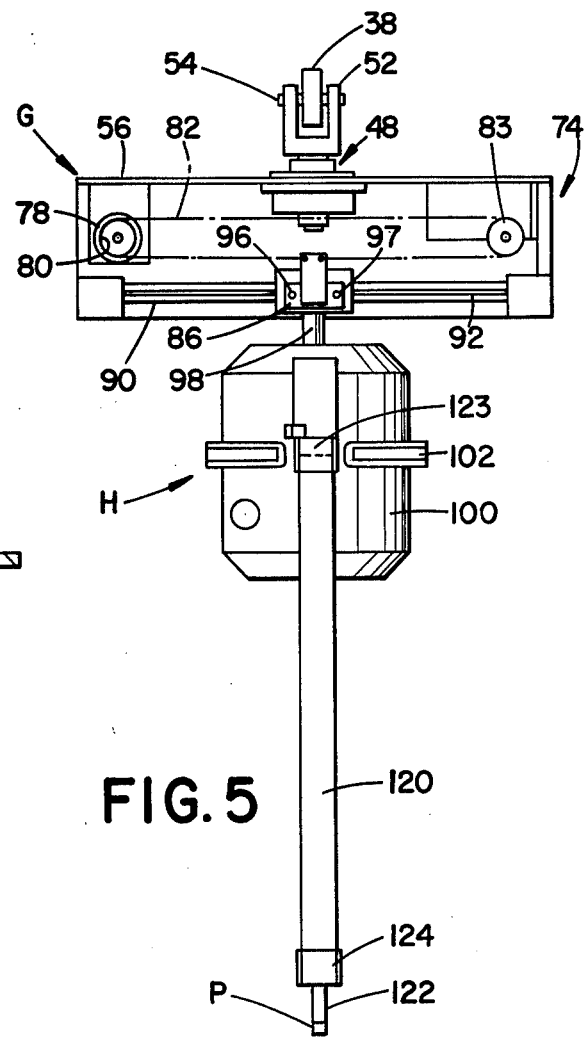
FIG. 5 is a front elevational view of the traversing mechanism shown in FIG. 1 with a portion thereof removed for ease of illustration; and, FIG. 6 is an enlarged view of a portion of the displacement assembly shown in FIG. 1.

Although a great variety of equipment may be attached to and depend from overhead arm assembly B, the preferred embodiment contemplates use of a manipulating assembly E adapted to move an ultrasonic probe in a single flat plane across or along a patient. As shown in FIGS. 1 and 5, displacement means G is attached to overhead arm assembly B by rotational means F. The displacement means includes a motor 76 coupled to a drive wheel 80 by an electric clutch 78. A continuous drive chain 82 is carried by wheel 80 and a companion wheel 83 and is connected to a flange 84 on a block or bracket 86. Block 86 slides on a rod 90 and convenient guide means such as a groove or track 92 for guiding the block along a linear path perpendicular to the axis of terminal arm 51. The guide means could alternatively comprise a cam follower or the like constrained between guide rods. Block 86 has a pair of detents which engage track 92. One detent 94 is best shown in FIG. 6 and comprises a sphere whose degree of engagement is set by a threaded shaft 96. The other detent is identical to detent 94 and is set by a threaded shaft 97 (FIG. 5). A suitable control (not shown) is provided for causing clutch 78 to engage and disengage. This control may advantageously include a displacement distance means for causing block 86 to be displaced a selectable or fixed incremental distance on each actuation of the clutch.

Referring to both FIGS. 1 and 5, a generally C-shaped arm bracket 98 connects the block to angular orientation selection means H and scan arm assembly I. A housing 100 connected with the arm bracket includes a handle 102 to facilitate positioning of the housing by the operator. Referring specifically to FIG. 1, angular orientation means H includes a pivot rod 104, a rotational rod 106 and a disc brake arrangement 108 to lock the angular rotation of rod 106 about the bracket 98. Rotational rod 106 allows orientation selection means H and scan arm assembly I to be selectively rotated thereabout in what is termed as a roll plane. A brake pad 110 attached to housing 100 is lightly in contact with one face of a brake disc 112 and a second brake pad 114 is movably engageable with the other face of brake disc 112 to selectively lock the rod 100 in a desired angular orientation within the rod plane. A screw handle 116 which threadably penetrates housing 100 and has brake pad 114 affixed to the innermost end thereof allows the operator to screw the pad firmly into contact with disc 112 to achieve such locking. A friction type of brake arrangement could also be used in place of disc brake arrangement 108.

Pivotally attached to rod 106 by a pin 117 is a multijointed scan arm assembly I. In the preferred embodiment, the scan arm assembly comprises three pivotally joined arms 118, 120 and 122. First scan arm 118 is constrained at one end by pin 117 to pivot about rod 106 only in a single scan plane. The orientation of the scan plane is dictated by the rotational orientation of rod portion 106. One end area of scan arm 120 is pivotally attached to the other end of first scan arm 118 by a pin 123. Third scan arm 122 is attached to the other or second end of the second scan arm at a pivot joint 124 and the outermost end of the third scan arm carries an ultrasonic probe P. The pivot connections at 123, 124 are such that third scan arm 122 is contrained to move only within the scan plane. Moreover, these pivot connections may, if desired, also include friction brakes similar to those discussed hereinabove. Alternately, for some applications, joint 124 may advantageously comprise a gimbal.

Second scan arm 120 has a section 125 which extends above pin 123 as viewed in FIG. 1 to a pivotal connection 128. A scan arm dynamic counterweight assembly which includes a connecting rod 130 extends between connection 128 and a pivot pin 132 in a lever arm 134. Lever arm 134 is pivotally attached at one end to first scan arm 118 by a pin 136 and has a biasing means such as a counterweight 138 disposed at the other end. Connecting rod 130 constrains lever arm 134 and arm 120 to a substantially parallel or other fixed relationship relative to each other.

Weight 138 with lever arm 134 provides a dynamic counterbalance which functions in a manner similar to that described above with reference to the dynamic counterbalance portion of assembly D. It will be noted that pivot connections 136, 123, 128 and 132 define a parallelogram with sides of a fixed length. Accordingly, this parallelogram constrains lever arm 134 to remain parallel to second scan arm 120.

Ultrasonic probe P may comprise a single one or an array of transducer elements used for ultrasonic diagnostic testing. Such probes are known and do not themselves comprise a part of the present invention. They produce ultrasonic sound waves which are broadcast parallel to the central axis of the third scan arm and receive ultrasonic echoes from interfaces in a patient. By coordinating the position and orientation of the probe with an electronic processing unit, the precise origin of the received ultrasonic echoes within the patient's body can be determined. The ultrasonic scanning device can then accurately produce an image of the sub-surface region of the patient.

In operation, overhead arm assembly B with attendant equipment is brought into close proximity with the patient who is positioned therebeneath. Normally, the patient lies horizontally on a platform or table so that a traverse section of his body can be examined. However, other orientations may also be used if necessary and/or desirable.

The operator then grasps handle 102 on means H for moving manipulating assembly E to the appropriate position and height for, in turn, positioning scan arm assembly I to make a proper scan. This appropriate position is such that the plane movement of the scan arm assembly is coplanar with the plane of interest in the patient. The appropriate height is that distance above the patient such that the operator can easily position probe P at a multiplicity of points along the line of intersection between the plane and the surface of the patient and then rock third scan arm 122 about pivot 124 at each point of contact. This action will be described in greater detail hereinafter.

As the operator swings manipulating assembly E into position, a number of movements occur. The overhead arm assembly B rotates in the yaw plane about pin 18. A second yaw plane rotation occurs in rotational connection F. Once positioned, friction brakes 24, 26 and 59 retain the manipulating assembly in this selected yaw plane orientation. Additionally, the operator rotates the scan arm assembly in the roll plane about pin 104 with the orientation of this roll plane retained by means of brake 108.

In selecting the height and the distance from column 10, the operator pivots arms 16, 38 and 51 in the pitch plane about pivot pins 20, 36 and 54. As discussed above, during the pitch plane positioning, orientation means C constrains the central axis of arm 51 to a vertical disposition. Once positioned, friction brakes 30, 40 help retain overhead arms 16, 38 and 51 in that position.

The ease with which the overhead arms can be moved and their stability in the selected position is increased by counter balance means D. As also discussed above, the pivoting of arm 16 pivot pin 20 varies the effective lever arm with which counterweight 60 is applied. Pivoting of arm 38 about pivot pin 36 relative to arm 16 varies the lever arm of dynamic counterweight 62. Proper selection of weights 60, 62 coupled with proper selection of the length of lever 64 will cause the manipulating assembly to appear or seem to be substantially weightless to the operator when it is being positioned to accommmodate a scan.

With the overall assembly properly positioned, the operator moves the transducer probe P along the intersection of the scan arm movement plane and the body surface of the patient. As the probe traverses the patient, the operator oscillates it about the point or area of patient contact so that the internal area of the patient can be "viewed" from a multiplicity of directions. Conventional ultrasonic image reconstruction equipment may be used for this purpose and such equipment does not itself form a part of the present invention. However, one type and arrangement of suitable equipment is shown and described in the article by Joseph Holmes, et al., "Ultrasonic Contact Scanner for Diagnostic Application," The American Journal of Medical Electronics, pp 147–152 (1965). The arrangement therein shown includes circuitry for monitoring the position and orientation of the transducer probe and for processing the ultrasonic echo signals to produce an image of the planar patient section examined.

After the first scan image is produced and recorded, the operator actuates clutch 78 arrangement of displacement assembly G for allowing motor 76 to move the plane of examination by a known increment to a new position. Because of the construction of assembly G as described in detail hereinabove, the plane of the new position is parallel to the plane of the original position. The scanning procedure is then repeated in this second plane and in as many further incrementally shifted planes as may be desired. This series of scans produces a series of images representing parallel sections of the patient.

It is understood that the present invention may be used to carry other work elements that require precise positioning and movement. For example, instead of using an ultrasonic transmitting and receiving probe, the system can carry an electron or laser welding unit for making precise welds, carry engraving tools or carry other precision equipment.

The above physical embodiment is presented only by way of example and not for purposes of limitation. The invention includes not only the above specific embodiment, but all the embodiments thereto as set forth in the claims as follows.

Having thus described the invention, it is now claimed:

1. An overhead arm assembly comprising:
   a. a base;
   b. a first arm means including a plurality of interconnected arm portions with one of said arm portions pivotally connected to said base, another of said arm portions having a central axis along its length and being connected adjacent one end thereof to a manipulative assembly; and
   c. said manipulative assembly comprising:
      i. multijointed scan arm assembly carrying a work element constrained for motion substantially within a single plane; and
      ii. positioning means connected to said first arm means for selectively determining the position of said scan arm assembly single plane, said positioning means includes displacement means for displacing said scan arm assembly single plane from an initial position to at least one second position substantially parallel to said initial position.

2. The overhead arm assembly of claim 1 wherein said positioning means further includes rotational means operably associated with said first arm means for allowing rotation of said arm assembly single plane about said central axis.

3. The overhead arm assembly of claim 1 wherein said displacement means includes a drive chain for selectively moving said multijointed scan arm assembly plane from said initial to said at least one second position and further includes drive means for intermittently driving said chain, whereby said scan arm assembly plane may be incrementally displaced between said initial and said at least one second positions.

4. The overhead arm assembly of claim 3 wherein said drive chain comprises a continuous chain disposed to have a pair of runs around at least two spaced apart pulleys, said runs being oriented substantially normal to said central axis.

5. The overhead arm assembly of claim 1 wherein said displacement means further includes a bracket selectively displaceable to a plurality of positions, said positioning means further including angular orientation means for selectively adjusting the angular orientation of said single plane about an orientation axis perpendicular to said central axis and disposed between said bracket and said multijointed scan arm assembly.

6. The overhead arm assembly of claim 5 wherein said displacement means further includes guide means interacting with said bracket for constraining said bracket to a substantially linear path of motion.

7. The overhead arm assembly of claim 1 wherein said positioning means includes angular orientation means connected to said multijointed scan arm assembly for selectively adjusting the angular orientation of said scan arm assembly single plane relative to said central axis.

8. An overhead arm assembly comprising:
   a. a base;
   b. a first arm means including a plurality of interconnected arm portions with one of said arm portions pivotally connected to said base, another of said arm portions having a central axis along its length and being connected adjacent one end thereof to a manipulative assembly; and
   c. said manipulative assembly comprising:
      i. a multijointed scan arm assembly comprising: a first scanning arm; a second scanning arm pivotally connected adjacent one end to said first scanning arm; and, a third scanning arm which includes a work element and which third scanning arm is pivotally connected to said second scanning arm along the length thereof from said second scanning arm one end; said first, second and third scanning arms constrained for motion substantially within a single plane; and,
      ii. positioning means connected to said first arm means and pivotally connected to said first scanning arm for selectively determining the position of said scan arm assembly single plane.

9. The overhead arm assembly of claim 8 wherein said multijointed arm scan assembly further includes a dynamic counterbalance comprising a lever pivotally connected to said first scanning arm, biasing means connected to said lever and connecting means for connecting said lever and said second scanning arm whereby said connecting means maintains a parallel relationship between said lever and said second scanning arm.

10. The overhead arm assembly of claim 8 wherein said work element comprises an ultrasonic probe means adapted to transmit ultrasonic energy into a patient and to receive ultrasonic echoes from within said patient.

11. The overhead assembly of claim 8 wherein said postioning means includes rotational means operably connected with said first arm means for rotating said multijoined scan arm assembly about said central axis; displacement means operably connected with said rotational means for displacing said multijointed scan arm assembly in a direction generally perpendicular to said central axis; and, angular orientation means operably connected with said displacement means for selectively adjusting the angular orientation of said single plane about an axis generally perpendicular to both the direction along which the displacement means displaces the multijointed scan arm assembly and said central axis.

12. An overhead arm assembly comprising:
   a. a base;
   b. a first arm means including a plurality of movably interconnected arm portions with one of said arm portions pivotally connected to said base, another of said arm portions having a central axis along its length, orientation means for controlling the orientation of said central axis relative to said base said orientation means comprising a plurality of interconnected orientation connecting links with one of said links pivotally connected to said base and another of said links pivotally connected to said another arm portion; and
   c. a manipulative assembly comprising:
      i. a multi-jointed scan arm assembly carrying a work element and constrained for motion substantially within a single plane; and,
      ii. positioning means connected to said another arm portion and said multijointed scan arm assembly for selectively determining the position of said single plane, whereby said first arm means adjusts the location and the positioning means adjusts the orientation relative to said base of said single plane.

13. An overhead arm assembly comprising:
   a. a base;
   b. a first arm means comprising:
      i. a first arm pivotally mounted adjacent one end thereof to said base;
      ii. a second arm pivotally mounted adjacent one end thereof adjacent to the other end of said first arm;
      iii. a third arm pivotally mounted adjacent one end thereof adjacent to the other end of said second arm; said third arm having a central axis along its length;
      iv. a dynamic counterbalancing means for applying a counterbalancing force to said first arm varying in response to the angular orientation of said second arm relative to said base; and
      v. orientation means for contraining the central axis of the third arm to a fixed angular orientation relative to said base; and
   c. a manipulative assembly connected adjacent the other end of said third arm, said manipulative assembly comprising;
      i. a multijointed scan arm assembly carrying an ultrasonic probe and constrained for motion in a single plane; and
      ii. positioning means operatively connected with said third arm and said multijointed scan arm assembly for selectively determining the position of said scan arm assembly single plane, said positioning means comprising rotational means for selectively allowing rotation of said scan arm assembly single plane about said central axis, displacement means for selectively displacing said scan arm assembly single plane from an initial position to substantially parallel positions, and angular orientation means for selectively adjusting the angular orientation of said scan arm assembly plane relative to said central axis.

* * * * *

UNITED STATES PATENT AND TRADEMARK OFFICE
CERTIFICATE OF CORRECTION

PATENT NO. : 4,196,630
DATED : April 8, 1980
INVENTOR(S) : Dale C. Rudolph

It is certified that error appears in the above—identified patent and that said Letters Patent is hereby corrected as shown below:

In the patent heading, the following patent assignment data is added following the line identified as [76] Inventor:

Assignee: Unirad Corporation
                   Englewood, Colorado

Signed and Sealed this

First Day of July 1980

[SEAL]

Attest:

SIDNEY A. DIAMOND

*Attesting Officer*      *Commissioner of Patents and Trademarks*